US012559758B2

(12) United States Patent
Thompson et al.

(10) Patent No.: US 12,559,758 B2
(45) Date of Patent: Feb. 24, 2026

(54) COMPOSITION FOR REGULATING PRODUCTION OF INTERFERING RIBONUCLEIC ACID

(71) Applicant: Wyvern Pharmaceuticals Inc., Calgary (CA)

(72) Inventors: Bradley G. Thompson, Calgary (CA); Jill Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

(21) Appl. No.: 19/300,113

(22) Filed: Aug. 14, 2025

(65) Prior Publication Data

US 2025/0369002 A1     Dec. 4, 2025

Related U.S. Application Data

(63) Continuation of application No. 18/518,177, filed on Nov. 22, 2023, now Pat. No. 12,435,338.

(51) Int. Cl.
| | |
|---|---|
| *C07H 21/02* | (2006.01) |
| *C12N 15/117* | (2010.01) |
| *C12N 15/86* | (2006.01) |

(52) U.S. Cl.
CPC ............ *C12N 15/117* (2013.01); *C12N 15/86* (2013.01); *C12N 2310/141* (2013.01); *C12N 2750/14143* (2013.01)

(58) Field of Classification Search
CPC ......................... C12N 15/113; C12N 2310/141
See application file for complete search history.

(56) References Cited

U.S. PATENT DOCUMENTS

| | | | |
|---|---|---|---|
| 11,085,055 B2 | 8/2021 | Mallol et al. | |
| 11,162,102 B2 | 11/2021 | Minshull et al. | |
| 11,530,423 B1 | 12/2022 | Thompson | |
| 11,873,505 B2 | 1/2024 | Thompson | |
| 12,018,274 B2 | 6/2024 | Thompson | |
| 12,134,770 B1 | 11/2024 | Thompson | |
| 2022/0220187 A1 | 7/2022 | Sabzevari | |
| 2022/0356489 A1 | 11/2022 | Thompson | |
| 2024/0026377 A1 | 1/2024 | Thompson | |

FOREIGN PATENT DOCUMENTS

| CA | 2721333 A1 | 10/2009 |
|---|---|---|

OTHER PUBLICATIONS

Broughton et al. (Molecular Cell, 64, 320-333, 2016 ).*
Wang et al. "Adeno-associated virus vector as a platform for gene therapy delivery". Nat Rev Drug Discov. May 2019;18(5):358-378. (Year: 2019).
NCBI Reference Sequence: NC_000009.12. *Homo sapiens* chromosome 9, GRCh38.p14 Primary Assembly. (gene="CD274", gene_ synonym=B7-H; B7H1; hPD-L1; PD-L1; PDCD1L1; PDCD1LG1; PDL1). Oct. 7, 2023. (Year: 2023).
Qiniou et al. Extraordinary diversity of the CD28/CTLA4 family across jawed vertebrates. Front. Immunol., Nov. 12, 2024. Sec. Comparative Immunology. vol. 15—2024. (Year: 2024).
NCBI Reference Sequence: NG_011502.1. *Homo sapiens* cytotoxic T-lymphocyte-associated protein 4 (CTLA4) on chromosome 2. Mar. 11, 2009. (Year: 2009).
NCBI Reference Sequence: NR_030784.1. *Homo sapiens* microRNA 155 (MIR155), microRNA. Nov. 24, 2009. (Year: 2009).
Vaddi et al. CTLA4 mRNA is downregulatA4 mRNA is downregulated by miR-155 in regulatory T cells, and reduced blood CTLA4 levels are associated with poor prognosis in metastatic melanoma patients. Front. Immunol. Apr. 30, 2023.Sec. Cancer Immunity and Immunotherapy. vol. 14—2023. (Year: 2023).
Yuasa et al. Low efficiency ID02 enzymes are conserved in lower vertebrates, whereas higher efficiency IDO1 enzymes are dispensable. FEBS Journal 282 (2015) 2735-2745. (Year: 2015).
GenBank: LM608503.1. TPA: *Homo sapiens* microRNA hsa-mir-153-1 precursor. Mar. 3, 2015. (Year: 2015).
GenBank: LM608504.1. TPA: *Homo sapiens* microRNA hsa-mir-153-2 precursor. Mar. 3, 2015. (Year: 2015).
NCBI Reference Sequence: NG_028155.1. *Homo sapiens* indoleamine 2,3-dioxygenase 1 (IDO1), RefSeqGene on chromosome 8. May 18, 2020. (Year: 2020).
Bottoni et al. "Targeting BTK through microRNA in chronic lymphocytic leukemia." Blood, The Journal of the American.
Christensen et al. "Recombinant adeno-associated virus-mediated microRNA delivery into the postnatal mouse brain reveals a role for miR-134 in dendritogenesis in vivo." Frontiers in neural circuits 3 (2010): 848.
Bofill-De Ros et al. "Guidelines for the optimal design of miRNA-based shRNAs." Methods 103 (2016): 157-166.
Tritschler et al. "Concepts and limitations for learning developmental trajectories from single cell genomics." Development 146.12 (2019): dev170506.
Ahmadzadeh et al. "BRAF mutation in hairy cell leukemia." Oncology reviews 8.2 (2014): 253.
Patton et al. "Biogenesis, delivery, and function of extracellular RNA." Journal of extracellular vesicles 4.1 (2015): 27494.

(Continued)

*Primary Examiner* — Amy Rose Hudson
(74) *Attorney, Agent, or Firm* — Gowling WLG (Canada) LLP

(57) ABSTRACT

Embodiments of the present disclosure relate to a composition that comprises a recombinant plasmid (RP) with a sequence of nucleic acids. The sequence comprise a start region, an end region and an insert positioned between the start region and the end region. The insert encodes for a sequence of micro interfering ribonucleic acid (miRNA) that may be complimentary to a sequence of target messenger RNA (mRNA) that encodes for translation of a target biomolecule. The miRNA can cause the target mRNA to be degraded or inactivated, thereby causing a decrease in bioavailability of the target biomolecule because it is degraded or inactivated by the miRNA, thereby decreasing the bioavailability of the target biomolecule. In some embodiments of the present disclosure, the target biomolecule is an immune checkpoint protein.

2 Claims, No Drawings

Specification includes a Sequence Listing.

(56)               References Cited

OTHER PUBLICATIONS

Clark et al. "Detection of BRAF splicing variants in plasma-derived cell-free nucleic acids and extracellular vesicles of melanoma patients failing targeted therapy therapies." Oncotarget 11.44 (2020): 4016.

Kondratov et al. "Direct head-to-head evaluation of recombinant adeno-associated viral vectors manufactured in human versus insect cells." Molecular Therapy 25.12 (2017): 2661-2675.

Nature (2010. Gene Expression. Scitable. Available online at Nature. com) <https://www.nature.com/scitable/topicpage/gene-expression-14121669> (2010).

Brutons Tyrosine Kinase Genbank Sequence (2023).

GenBank EGFR Sequence (2023).

GenBank EGF Sequence (2023).

NCBI search results for SEQ ID No. 5 (2024).

NCBI Nucleotide Sequence ALK Lingand, search performed Dec. 26, 2024 (2023).

NCBI Nucleotide Sequence ALK Receptor, search performed Dec. 26, 2024 (2023).

NCBI Nucleotide Sequence for PARP, search performed Dec. 26, 2024 (2024).

GenBank FLT3 Sequence (2024).

Barnum KJ, O'Connell MJ. Cell cycle regulation by checkpoints. Methods Mol Biol. 2014;1170:29-40. doi: 10.1007/978-1-4939-0888-2_2. PMID: 24906307; PMCID: PMC4990352. (Year: 2014).

O'Brien J, Hayder H, Zayed Y, Peng C. Overview of MicroRNA Biogenesis, Mechanisms of Actions, and Circulation. Front Endocrinol (Lausanne). Aug. 3, 2018;9:402. doi: 10.3389/fendo.2018.00402. PMID: 30123182; PMCID: PMC6085463. (Year: 2018).

Zhang S, Cheng Z, Wang Y, Han T. The Risks of miRNA Therapeutics: In a Drug Target Perspective. Drug Des Devel Ther. Feb. 22, 2021;15:721-733. doi: 10.2147/DDDT.S288859. Erratum in: Drug Des Devel Ther. Mar. 30, 2021;15:1423. doi: 10.2147/DDDT. S310264. PMID: 33654378; PMCID: PMC7910153. (Year: 2021).

Defining checkpoint molecules: Zhang, Y., Zheng, J. (2020). Functions of Immune Checkpoint Molecules Beyond Immune Evasion.

In: Xu, J. (eds) Regulation of Cancer Immune Checkpoints. Advances in Experimental Medicine and Biology, vol. 1248. Springer, Singapore. (Year: 2020).

Kozomara A, Birgaoanu M, Griffiths-Jones S. miRBase: from microRNA sequences to function. Nucleic Acids Res. Jan. 8, 2019;47(D1):D155-D162. doi: 10.1093/nar/gky1141. PMID: 30423142; PMCID: PMC6323917. (Year: 2018).

Juppner H. Functional properties of the PTH/PTHrP receptor. Bone. Aug. 1995; 17(2 Suppl):39S-42S. doi: 10.1016/8756-3282(95)00206-s. PMID: 8579896. (Year: 1995).

Ha M, Pang M, Agarwal V, Chen ZJ. Interspecies regulation of microRNAs and their targets. Biochim Biophys Acta. Nov. 2008; 1779 (11):735-42. doi: 10.1016/j.bbagrm.2008.03.004. Epub Mar. 25, 2008. PMID: 18407843; PMCID: PMC2586835. (Year: 2008).

Ha et al. Interspecies Regulation of MicroRNAs and Their Targets, Biochim Biophys Acta. Nov. 2008; 1779(11): 735-74. (Year: 2008).

Ahmad et al .Adaptive selection in the evolution of programmed cell death-1 and its ligands in vertebrates. Aging (Albany NY).Feb. 11, 2020;12(4):3516-3557. (Year: 2020).

Lam et al. 2015. siRNA Versus miRNA as Therapeutics for Gene Silencing. Molec. Ther. Nuc. Ac. 4:e252. doi: 10.1038/mtna.2015. 23. (Year: 2015).

Ying et al. 2008. The MicroRNA (miRNA): Overview of the RNA Genes that Modulate Gene Function. Mol. Biotechnol. 38:257-268. doi: 10.1007/s12033-007-9013-8 (Year: 2008).

Gorski, S., Vogel, J. & Doudna, J. RNA-based recognition and targeting: sowing the seeds of specificity. Nat Rev Mol Cell Biol 18, 215-228 (2017). (Year: 2017).

Denzler R et al. Impact of MicroRNA Levels, Target-Site Complementarity, and Cooperativity on Competing Endogenous RNA-Regulated Gene Expression. Mol Cell. Nov. 3, 2016;64(3):565-579. doi: 10.1016/j.molcel.2016.09.027 (Year: 2016).

Van den Berg, et al., pp. 1-12, Molecular Therapy—Nucleic Acids, vol. 5, 2016 (Year: 2016).

Liu et al. Clinical value of CTLA4-associated microRNAs combined with inflammatory factors in the diagnosis of non-small cell lung cancer. Annals of Clinical Biochemistry: International Journal of Laboratory Medicine. 2020;57 (2):151-161. (Year: 2020).

Lundstrom K.. Viral Vectors in Gene Therapy: Where Do We Stand in 2023? Viruses. Mar. 7, 2023;15(3):698. (Year: 2023).

* cited by examiner

SEQUENCE LISTING

```
Sequence total quantity: 11
SEQ ID NO: 1              moltype = DNA  length = 5883
FEATURE                  Location/Qualifiers
source                   1..5883
                         mol_type = other DNA
                         organism = synthetic construct
SEQUENCE: 1
aatcaacctc tggattacaa aatttgtgaa agattgactg gtattcttaa ctatgttgct   60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aaccccact   240
ggttggggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgcc taagcttatc  600
gataccgtcg agatctaact tgtttattgc agcttataat ggttacaaat aaagcaatag  660
catcacaaat ttcacaaata aagcattttt ttcactgcat tctagttgtg gtttgtccaa  720
actcatcaat gtatcttatc atgtctggat ctcgacctcg actagagcat ggctacgtag  780
ataagtagca tggcgggtta atcattaact acaaggaacc cctagtgatg gagttggcca  840
ctccctctct gcgcgctcgc tcgctcactg aggccgggcg accaaaggtc gcccgacgcc  900
cgggctttgc ccgggcggcc tcagtgagcg agcgagcgcg cagctggcgt aatagcgaag  960
aggcccgcac cgatcgccct tcccaacagt tgcgcagcct gaatggcgaa tggcgattcc  1020
gttgcaatgg ctggcggtaa tattgttctg gatattacca gcaaggccga tagtttgagt  1080
tcttctactc aggcaagtga tgttattact aatcaaagaa gtattgcgac aacggttaat  1140
ttgcgtgatg acagactct tttactcggt ggcctcactg attataaaaa cacttctcag  1200
gattctggcg taccgttcct gtctaaaatc cctttaatcg gcctcctgtt tagctcccgc  1260
tctgattcta acgaggaaag cacgttatac gtgctcgtca aagcaaccat agtacgcgc   1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg ctccctttta gggttccgat ttagtgcttt  1500
acggcacctc gaccccaaaa aacttgatta gggtgatggt tcacgtagtg ggccatcgcc  1560
ctgatagacg gtttttcgcc ctttgacgtt ggagtccacg ttctttaata gtggactctt  1620
gttccaaact ggaacaacac tcaacccttat ctcggtctat tcttttgatt tataagggat  1680
tttgccgatt tcggcctatt ggttaaaaaa tgagctgatt taacaaaaat ttaacgcgaa  1740
```

-continued

```
ttttaacaaa atattaacgt ttacaattta aatatttgct tatacaatct tcctgttttt   1800
ggggctttc tgattatcaa ccggggtaca tatgattgac atgctagttt tacgattacc     1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt taaaatatat gagggttcta aaaatttta tccttgcgtt    2100
gaaataaagg cttctcccgc aaaagtatta cagggtcata atgttttgg tacaaccgat     2160
ttagctttat gctctgaggc tttattgctt aattttgcta attctttgcc ttgcctgtat    2220
gatttattgg atgttggaat tcctgatgcg gtattttctc cttacgcatc tgtgcggtat    2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc    2460
atcaccgaaa cgcgcgagac gaaagggcct cgtgatacgc ctatttttat aggttaatgt    2520
catgataata atggtttctt agacgtcagg tggcactttt cggggaaatg tgcgcggaac   2580
ccctatttgt ttattttct aaatacattc aaatatgtat ccgctcatga gacaataacc     2640
ctgataaatg cttcaataat attgaaaaag gaagagtatg agtattcaac atttccgtgt    2700
cgcccttatt cccttttttg cggcattttg ccttcctgtt tttgctcacc cagaaacgct    2760
ggtgaaagta aaagatgctg aagatcagtt gggtgcacga gtgggttaca tcgaactgga    2820
tctcaacagc ggtaagatcc ttgagagttt tcgccccgaa gaacgttttc caatgatgag    2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
ttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggcctttt   4320
acggttcctg gccttttgct ggccttttgc tcacatgttc tttcctgcgt tatccctga    4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcggcg acctttggtc gcccggcctc agtgagcgag    4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgacccccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tcccccccct   5100
ccccacccc aattttgtat ttatttattt tttaattatt ttgtgcagcg atggggggcgg   5160
ggggggggg gggcgcgcgc caggcgggc ggggcgggc gaggggcggg gcggggcgag      5220
gcggagaggt gcggcggcag ccaatcagag cggcgcgctc cgaaagtttc ctttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg gcgagcgctg ccacgtcaga cgaagggcgc agcgagcgtc   5520
ctgatccttc cgcccgacg ctcaggacag cggcccgctg ctcataagac tcggccttag    5580
aaccccagta tcagcagaag gacattttag gacgggactt gggtgactct agggcactgg    5640
ttttctttcc agagagcgga acaggcgagg aaaagtagtc ccttctcggc gattctgcgg    5700
agggatctcc gtggggcggt gaacgccgat gatgcctcta ctaaccatgt tcatgttttc   5760
tttttttttc tacaggtcct gggtgacgaa cagggtaccg ccaccatggc caccggctct    5820
cgcacaagcc tgctgctggc tttcggactg ctgtgcctgc cttggctcca ggagggctcc    5880
gcc                                                                  5883
```

```
SEQ ID NO: 2            moltype = DNA  length = 460
FEATURE                 Location/Qualifiers
source                  1..460
                        mol_type = other DNA
                        organism = synthetic construct
SEQUENCE: 2
gctagcatcg ataccgtcgc tatgtgctgg aggcttgctg aaggctgtat gctgtaccta   60
agaactgcat cctggccgtt ttggcctctg actgacggc aggatggttc ttaggtacag     120
```

-continued

```
gacacaaggc ctgttactag cactcacatg gaacaaatgg cctctagcct ggaggcttgc   180
tgaaggctgt atgctgtcgt aaagccaata ggttagtccc gttttggcct ctgactgacg   240
ggactaacct tggctttacg acaggacaca aggcctgtta ctagcactca catggaacaa   300
atggcctcta gcctggaggc ttgctgaagg ctgtatgctg agagagaccg caaattaccg   360
gacggttttg gcctctgact gaccgtcctg taatgcggtc tctctcagga cacaaggcct   420
gttactagca ctcacatgga acaaatggcc tctctagaat                          460

SEQ ID NO: 3             moltype = DNA   length = 456
FEATURE                  Location/Qualifiers
source                   1..456
                         mol_type = other DNA
                         organism = synthetic construct
SEQUENCE: 3
gctagcatcg ataccgtcgc tatgtgctgg aggcttgctg aaggctgtat gctgagagac    60
ttacttgtag atgctgcgtt ttggcctctg actgacgcag catctaagta agtctctcag   120
gacacaaggc ctgttactag cactcacatg gaacaaatgg cctctagcct ggaggcttgc   180
tgaaggctgt atgctgacta tttcatcata ctctcacccg ttttggcctc tgactgacgg   240
gtgagagtga tgaaatagtc aggacacaag gcctgttact agcactcaca tggaacaaat   300
ggcctctagc ctggaggctt gctgaaggct gtatgctgat atgaatgaca atcacagccg   360
agttttggcc tctgactgac gtggctgtga gtcattcata tcaggacaca aggcctgtta   420
ctagcactca catggaacaa atggcctctc tagaat                             456

SEQ ID NO: 4             moltype = DNA   length = 456
FEATURE                  Location/Qualifiers
source                   1..456
                         mol_type = other DNA
                         organism = synthetic construct
SEQUENCE: 4
gctagcatcg ataccgtcgc tatgtgctgg aggcttgctg aaggctgtat gctgacaatc    60
aacattggca gtagctcgtt ttggcctctg actgacgagc tactgcatgt tgattgtcag   120
gacacaaggc ctgttactag cactcacatg gaacaaatgg cctctagcct ggaggcttgc   180
tgaaggctgt atgctgaata agcctttatc catagtcccg ttttggcctc tgactgacgg   240
gactatggaa aggcttattc aggacacaag gcctgttact agcactcaca tggaacaaat   300
ggcctctagc ctggaggctt gctgaaggct gtatgctgac aactgtctca aattactgct   360
cgttttggcc tctgactgac gagcagtaat gagacagttg tcaggacaca aggcctgtta   420
ctagcactca catggaacaa atggcctctc tagaat                             456

SEQ ID NO: 5             moltype = DNA   length = 456
FEATURE                  Location/Qualifiers
source                   1..456
                         mol_type = other DNA
                         organism = synthetic construct
SEQUENCE: 5
gctagcatcg ataccgtcgc tatgtgctgg aggcttgctg aaggctgtat gctgtcactc    60
acctttgtgc agaagacgtt ttggcctctg actgacgtct tctgcaaagg tgagtgcacg   120
gacacaaggc ctgttactag cactcacatg gaacaaatgg cctctagcct ggaggcttgc   180
tgaaggctgt atgctggttc ttagcctatc tcaagtacg ttttggcctc tgactgacgg    240
tacttgagag gctaagacac aggacacaag gcctgttact agcactcaca tggaacaaat   300
ggcctctagc ctggaggctt gctgaaggct gtatgctggt ctatgtctaa attccagcag   360
cgttttggcc tctgactgac gctgctggaa tagacatgac acaggacaca aggcctgtta   420
ctagcactca catggaacaa atggcctctc tagaat                             456

SEQ ID NO: 6             moltype = DNA   length = 458
FEATURE                  Location/Qualifiers
source                   1..458
                         mol_type = other DNA
                         organism = synthetic construct
SEQUENCE: 6
gctagcatcg ataccgtcgc tatgtgctgg aggcttgctg aaggctgtat gctgctcact    60
tgaattgctt accgctccgt tttggcctct gactgacgga gcggtaagat tcaagtgagc   120
aggacacaag gcctgttact agcactcaca tggaacaaat ggcctctagc ctggaggctt   180
gctgaaggct gtatgctgtg tctgatccta tctcaagtag cgtttggcc tctgactgac    240
gctacttgag aggctaagac acaggacaca aggcctgtta ctagcactca catggaacaa   300
atggcctcta gcctggaggc ttgctgaagg ctgtatgctg atgtttccgg gaaacagtga   360
ctcgttttgg cctctgactg acgattcact gtcccggaaa catcaggaca caaggcctgt   420
tactagcact cacatggaac aaatggcctc tctagaat                           458

SEQ ID NO: 7             moltype = DNA   length = 6343
FEATURE                  Location/Qualifiers
source                   1..6343
                         mol_type = other DNA
                         organism = synthetic construct
SEQUENCE: 7
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccccact   240
ggttggggca ttgccaccac ctgtcagctc ctttccggga ctttcgcttt ccccctccct   300
attgccacgg cggaactcat cgccgcctgc cttgcccgct gctggacagg ggctcggctg   360
```

-continued

```
ttgggcactg acaattccgt ggtgttgtcg gggaaatcat cgtcctttcc ttggctgctc    420
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatcctcc cttttgggccg cctccccgcc taagcttatc    600
gataccgtcg agatctaact tgtttattgc agcttataat ggttacaaat aaagcaatag    660
catcacaaat ttcacaaata aagcattttt ttcactgcat tctagttgtg gtttgtccaa    720
actcatcaat gtatcttatc atgtctggat ctcgacctcg actagagcat ggctacgtag    780
ataagtagca tggcgggtta atcattaact acaaggaacc cctagtgatg gagttggcca    840
ctccctctct gcgcgctcgc tcgctcactg aggccgggcg accaaaggtc gcccgacgcc    900
cgggctttgc ccgggcggcc tcagtgagcg agcgagcgcg cagctggcgt aatagcgaag    960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggcg taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg gctcccttta gggttccgat ttagtgcttt   1500
acggcacctc gaccccaaaa aacttgatta gggtgatggt tcacgtagtg ggccatcgcc   1560
ctgatagacg gtttttcgcc ctttgacgtt ggagtccacg ttctttaata gtggactctt   1620
gttccaaact ggaacaacac tcaaccctat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt taaaatatat gagggttcta aaaattttta tccttgcgtt   2100
gaaataaagg cttctcccgc aaaagtatta cagggtcata atgtttttgg tacaaccgat   2160
ttagctttat gctctgaggc tttattgctt aattttgcta attctttgcc ttgcctgtat   2220
gatttattgg atgttggaat tcctgatgcg gtatttttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcactttt cggggaaatg tgcgcggaac   2580
ccctatttgt ttatttttct aaatacattc aaatatgtat ccgctcatga gacaataacc   2640
ctgataaatg cttcaataat attgaaaaag gaagagtatg agtattcaac atttccgtgt   2700
cgcccttatt cccttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
ttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aagatcaaa ggatcttctt gagatccttt    3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga aaaggcgga    4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggccttttt   4320
acggttcctg gccttttgct ggccttttgc tcacatgttc tttcctgcgt tatccctga    4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgacccccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgcccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tcccccccct   5100
```

```
ccccaccccc aattttgtat ttatttattt tttaattatt ttgtgcagcg atggggcgg      5160
ggggggggg gggcgcgcgc caggcggggc ggggcggggc gagggcgggg gcggggcgag      5220
gcggagaggt gcggcggcag ccaatcagag cggcgcgctc cgaaagtttc cttttatggc      5280
gaggcggcgg cggcggcggc cctataaaaa gcgaagcgcg cggcgggcgg gagtcgctgc      5340
gcgctgcctt cgccccgtgc cccgctccgc cgccgcctcg cgccgcccgc cccggctctg      5400
actgaccgcg ttactaaaac aggtaagtcc ggcctccgcg ccgggttttg gcgcctcccg      5460
cgggcgcccc cctcctcacg gcgagcgctc ccacgtcaga cgaagggcgc agcgagcgtc      5520
ctgatccttc cgcccggacg ctcaggacag cggcccgctg ctcataagac tcggccttag      5580
aaccccagta tcagcagaag gacattttag gacgggactt gggtgactct agggcactgg      5640
ttttctttcc agagagcgga acaggcgagg aaaagtagtc ccttctcggc gattctgcgg      5700
agggatctcc gtggggcggt gaacgccgat gatgcctcta ctaaccatgt tcatgttttc      5760
ttttttttttc tacaggtcct gggtgacgaa cagggtaccg ccaccatggc caccggctct      5820
cgcacaagcc tgctgctggc tttcggactg ctgtgcctgc cttggctcca ggagggctcc      5880
gccgctagca tcgataccgt cgctatgtgc tggaggctg ctgaaggctg tatgctgtac      5940
ctaagaactg catcctggcc gttttggcct ctgactgacg gccaggatgg ttcttaggta      6000
caggacacaa ggcctgttac tagcactcac atggaacaaa tggcctctag cctggaggct      6060
tgctgaaggc tgtatgctgt cgtaaagcca ataggttagt cccgttttgg cctctgactg      6120
acgggactaa ccttggcttt acgacaggac acaaggccgt ttactagcac tcacatggaa      6180
caaatggcct ctagcctgga ggcttgctga aggctgtatg ctgagagaga ccgcaaatta      6240
ccggacggtt ttggcctctg actgaccgtc ctgtaatgcg gtctctctca ggacacaagg      6300
cctgttacta gcactcacat ggaacaaatg gcctctctag aat                        6343
```

```
SEQ ID NO: 8              moltype = DNA   length = 6339
FEATURE                   Location/Qualifiers
source                    1..6339
                          mol_type = other DNA
                          organism = synthetic construct
SEQUENCE: 8
aatcaacctc tggattacaa aatttgtgaa agattgactg gtattcttaa ctatgttgct      60
ccttttacgc tatgtggata cgctgcttta atgcctttgt atcatgctat tgcttcccgt      120
atggctttca ttttctcctc cttgtataaa tcctggttgc tgtctcttta tgaggagttg      180
tggcccgttg tcaggcaacg tggcgtggt tgcactgtgt ttgctgacgc aaccccact      240
ggttgggca ttgccaccac ctgtcagctc cctttccggga cttttcgcttt ccccctccct      300
attgccacgg cggaactcat cgccgcctgc cttgcccgct gctggacagg ggctcggctg      360
ttgggcactg acaattccgt ggtgttgtcg gggaaatcat cgtcctttcc ttggctgctc      420
gcctgtgttg ccacctggat tctgcgcggg acgtccttct gctacgtccc ttcggccctc      480
aatccagcgg accttccttc ccgcggcctg ctgccggctc tgcggcctct tccgcgtctt      540
cgccttcgcc ctcagacgag tcggatctcc cttttgggccg cctccccgcc taagcttatc      600
gataccgtcg agatctaact tgtttattgc agcttataat ggttacaaat aaagcaatag      660
catcacaaat ttcacaaata aagcatttt ttcactgcat tctagttgtg gtttgtccaa      720
actcatcaat gtatcttatc atgtctggat ctcgacctcg actagagcat ggctacgtag      780
ataagtagca tggcgggtta atcattaact acaaggaacc cctagtgatg gagttggcca      840
ctccctctct gcgcgctcgc tcgctcactg aggccgcggg accaaaggtc gcccgacgcc      900
cgggctttgc ccgggcggcc tcagtgagcg agcgagcgcg cagctggcgt aatagcgaag      960
aggcccgcac cgatcgccct tcccaacagt tgcgcagcct gaatggcgaa tggcgattcc      1020
gttgcaatgg ctggcggtaa tattgttctg gatattacca gcaaggccga tagtttgagt      1080
tcttctactc aggcaagtga tgttattact aatcaaagaa cgttaat      1140
ttgcgtgatg gacagactct tttactcggt ggcctcactg attataaaaa cacttctcag      1200
gattctggcg taccgttcct gtctaaaatc cctttaatcg gcctcctgtt tagctcccgc      1260
tctgattcta acgaggaaag cacgttatac gtgctcgtca aagcaaccat agtacgcgcc      1320
ctgtagcggc gcattaagcg cggcgggtgt ggtggttacg cgcagcgtga ccgctacact      1380
tgccagcgcc ctagcgcccg ctcctttcgc tttcttccct tcctttctcg ccacgttcgc      1440
cggctttccc cgtcaagctc taaatcgggg gctcccttta gggttccgat ttagtgcttt      1500
acggcacctc gaccccaaaa aacttgatta gggtgatggt tcacgtagtg ggccatcgcc      1560
ctgatagacg gtttttcgcc ctttgacgtt ggagtccacg ttctttaata gtggactctt      1620
gttccaaact ggaacaacac tcaaccctat ctcggtctat tcttttgatt tataagggat      1680
tttgccgatt tcggcctatt ggttaaaaaa tgagctgatt taacaaaaat ttaacgcgaa      1740
ttttaacaaa atattaacgt ttacaattta aatatttgct tatacaatct tcctgttttt      1800
ggggcttttc tgattatcaa ccggggtaca tatgattgac atgctagttt tacgattacc      1860
gttcatcgat tctcttgttt gctccagact ctcaggcaat gacctgatag cctttgtaga      1920
gacctctcaa aaatagctac cctctccggc atgaatttat cagctagaac ggttgaatat      1980
catattgatg gtgatttgac tgtctccggc ctttctcacc cgtttgaatc tttacctaca      2040
cattactcag gcattgcatt taaaatatat gagggttcta aaaattttta tccttgcgtt      2100
gaaataaagg cttctcccgc aaaagtatta cagggtcata atgtttttgg tacaaccgat      2160
ttagctttat gctctgaggc tttattgctt aattttgcta attctttgcc ttgcctgtat      2220
gatttattgg atgttggaat tcctgatgcg gtatttctc cttacgcatc tgtgcggtat      2280
ttcacaccgc atatggtgca ctctcagtac aatctgctct gatgccgcat agttaagcca      2340
gccccgacac ccgccaacac ccgctgacgc gccctgacgg gcttgtctgc tcccggcatc      2400
cgcttacaga caagctgtga ccgtctccgg gagctgcatg tgtcagaggt tttcaccgtc      2460
atcaccgaaa cgcgcgagac gaaagggcct cgtgatacgc ctatttttat aggttaatgt      2520
catgataata atggtttctt agacgtcagg tggcacttt cggggaaatg tgcgcggaac      2580
ccctattgt ttattttct aaatacattc aaatatgtat ccgctcatga caataacc      2640
ctgataaatg cttcaataat attgaaaaag gaagagtatg agtattcaac atttccgtgt      2700
cgcccttatt cccttttttg cggcattttg ccttcctgtt tttgctcacc cagaaacgct      2760
ggtgaaagta aaagatgctg aagatcagtt gggtgcacga gtgggttaca tcgaactgga      2820
tctcaacagc ggtaagatcc ttgagagttt tcgccccgaa gaacgttttc caatgatgag      2880
cacttttaaa gttctgctat gtggcgcggt attatcccgt attgacgccg ggcaagagca      2940
actcggtcgc cgcatacact attctcagaa tgacttggtt gagtactcac cagtcacaga      3000
aaagcatctt acggatggca tgacagtaag agaattatgc agtgctgcca taaccatgag      3060
```

```
tgataacact gcggccaact tacttctgac aacgatcgga ggaccgaagg agctaaccgc   3120
ttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctcacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc ttttttgataa tctcatgacc aaaatcccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagatacta cagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggcctttt   4320
acggttcctg gccttttgct ggccttttgc tcacatgttc tttcctgcgt tatcccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgga   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg cccgcctgg ctgaccgccc aacgaccccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgcccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tcccccccct   5100
ccccaccccc aatttgtat ttatttattt tttaattatt ttgtgcagcg atggggggcgg   5160
gggggggggg gggcgcgcgc caggcggggc ggggcggggc gaggggcggg gcggggcgag   5220
gcggagaggt gcggcggcag ccaatcagag cggcgcgctc cgaaagtttc cttttatggc   5280
gaggcggcgg cggcggcggc cctataaaaa gcgaagcgcg cggcggggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg gcgagcgctg ccacgtcaga cgaagggcgc agcgagcgtc   5520
ctgatccttc cgcccggacg ctcaggacag cggcccgctg ctcataagac tcggccttag   5580
aaccccagta tcagcagaag gacattttag gacgggactt gggtgactct agggcactgg   5640
ttttctttcc agagagcgga acaggcgagg aaaagtagtc ccttctcggc gattctgcgg   5700
agggatctcc gtggggcggt gaacgccgat gatgcctcta ctaaccatgt tcatgttttc   5760
tttttttttc tacaggtcct gggtgacgaa cagggtaccg ccaccatggc caccggctct   5820
cgcacaagcc tgctgctggc tttcggactg ctgtgcctga cttgggctcca ggagggctcc   5880
gccgctagca tcgataccgt cgctatgtgc tggaggcttg ctgaaggctg tatgctgaga   5940
gacttacttg tagatgctgc gttttggcct ctgactgacg cagcatctaa gtaagtctct   6000
caggacacaa ggcctgttac tagcactcac atggaacaaa tggcctctag cctggaggct   6060
tgctgaaggc tgtatgctga ctatttcatc atactctcac ccgtttttgc ctctgactga   6120
cgggtgagag tgatgaaata gtcaggacac aaggcctgtt actagcactc acatggaaca   6180
aatggcctct agcctggagg cttgctgaag gctgtatgct gatatgaatg acaatcacag   6240
ccgagttttg gcctctgact gacgtggctg tgagtcattc atatcaggac acaaggcctg   6300
ttactagcac tcacatggaa caaatggcct ctctagaat                          6339

SEQ ID NO: 9          moltype = DNA   length = 6339
FEATURE               Location/Qualifiers
source                1..6339
                      mol_type = other DNA
                      organism = synthetic construct
SEQUENCE: 9
aatcaacctc tggattacaa aatttgtgaa agattgactg gtattcttaa ctatgttgct   60
ccttttacgc tatgtggata cgctgcttta atgcctttgc atcatgctat tgcttccgt   120
atggctttca ttttctcctc cttgtataaa tcctggttgc tgtctctttta tgaggagttg   180
tggcccgttg tcaggcaacg tggcgtggtg tgcactgtgt ttgctgacgc aacccccact   240
ggttggggca ttgccaccac ctgtcagctc ctttccggga ctttcgcttt ccccctccct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg actagagcat ggctacgtag   780
ataagtagca tggcgggtta tcattaact acaaggaacc cctagtgatg gagttggcca   840
ctccctctct gcgcgctcgc tcgctcactg aggccgggcg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
```

-continued

```
gttgcaatgg ctggcggtaa tattgttctg gatattacca gcaaggccga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggcg taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg gctcccttta gggttccgat ttagtgcttt   1500
acggcacctc gaccccaaaa aacttgatta gggtgatggt tcacgtagtg ggccatcgcc   1560
ctgatagacg gtttttcgcc ctttgacgtt ggagtccacg ttctttaata gtggactctt   1620
gttccaaact ggaacaacac tcaaccctat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt taaaatatat gagggttcta aaattttta tccttgcgtt   2100
gaaataaagg cttctcccgc aaaagtatta caggggtcata atgttttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctattttat aggttaatgt   2520
catgataata atggtttctt agacgtcagg tggcacttt cgggaaaatg tgcgcggaac   2580
ccctatttgt ttatttttct aaatacattc aaatatgtat ccgctcatga gacaataacc   2640
ctgataaatg cttcaataat attgaaaaag gaagagtatg agtattcaac atttccgtgt   2700
cgcccttatt cccttttttg cggcattttg ccttcctgtt tttgctcacc cagaaacgct   2760
ggtgaaagta aaagatgctg aagatcagtt gggtgcacga gcgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
tttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggcctttt   4320
acggttcctg gccttttgct ggccttttgc tcacatgttc tttcctgcgt tatccctga   4380
ttctgtggat aaccgtatta ccgcctttga gtgagctgat accgctcgcc gcagccgaac   4440
gaccgagcgc agcgagtcag tgagcgagga gcggaagag cgcccaatac gcaaaccgcc   4500
tctccccgcg cgttggccga ttcattaatg cagcagctgc gcgctcgctc gctcactgag   4560
gccgcccggg caaagccggg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgc ctgaccgccc aacgacccc   4800
gcccattgac gtcaataatg acgtatgttc ccatagtaac acgcataggt actttccatt   4860
gacgtcaatg ggtggagtat ttacggtaaa ctgcccactt ggcagtacat caagtgtatc   4920
atatgccaag tacgccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tcccccccc   5100
cccaccccc aattttgtat ttatttattt tttaattatt ttgtgcagcg atgggggcgg   5160
gggggggggg gggcgcgcgc caggcggggc ggggcggggc gaggggcggg gcggggcgag   5220
gcggagaggt gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggctctg gtgcccccg   5460
cgggcgcccc cctcctcacg gcgagcgctg ccacgtcaga cgaagggcgc agcgagcgtc   5520
ctgatccttc cgcccggacg ctcaggacag cggcccgctg ctcataagac tcggccttag   5580
aaccccagta tcagcagaag gacattttag gacgggactt gggtgactct agggcactgg   5640
ttttctttcc agagagcgga acaggcgagg aaaagtagtc cttctcggc gattctgcgg   5700
agggatctcc gtggggcggt gaacgccgat gatgcctcta ctaaccatgt tcatgtttc   5760
```

```
tttttttttc tacaggtcct gggtgacgaa cagggtaccg ccaccatggc caccggctct  5820
cgcacaagcc tgctgctggc tttcggactg ctgtgcctgc cttggctcca ggagggctcc  5880
gccgctagca tcgataccgt cgctatgtgc tggaggcttg ctgaaggctg tatgctgaca  5940
atcaacattg gcagtagctc gttttggcct ctgactgacg agctactgca tgttgattgt  6000
caggacacaa ggcctgttac tagcactcac atggaacaaa tggcctctag cctggaggct  6060
tgctgaaggc tgtatgctga ataagccttt atccatagtc ccgtttggc ctctgactga    6120
cgggactatg gaaaggctta ttcaggacac aaggcctgtt actagcactc acatggaaca  6180
aatggcctct agcctggagg cttgctgaag gctgtatgct gacaactgtc tcaaattact  6240
gctcgttttg gcctctgact gacgagcagt aatgagacag ttgtcaggac acaaggcctg  6300
ttactagcac tcacatggaa caaatggcct ctctagaat                         6339
```

```
SEQ ID NO: 10           moltype = DNA   length = 6339
FEATURE                 Location/Qualifiers
source                  1..6339
                        mol_type = other DNA
                        organism = synthetic construct
SEQUENCE: 10
aatcaacctc tggattacaa aatttgtgaa agattgactg gtattcttaa ctatgttgct  60
cctttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aaccccact   240
ggttggggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgccgcgtct tttcgtctt    540
cgccttcgcc ctcagacgag tcggatctcc ctttgggccg cctccccgcc taagcttatc  600
gataccgtcg agatctaact tgtttattgc agcttataat ggttacaaat aaagcaatag  660
catcacaaat ttcacaaata aagcattttt ttcactgcat tctagttgtg gtttgtccaa  720
actcatcaat gtatcttatc atgtctggat ctcgacctcg actagagcat ggctacgtag  780
ataagtagca tggcgggtta atcattaact acaaggaacc cctagtgatg gagttggcca  840
ctccctctct gcgcgctcgc tcgctcactg aggccgggcg accaaaggtc gcccgacgcc  900
cgggctttgc ccgggcggcc tcagtgagcg agcgagcgcg cagctggcgt aatagcgaag  960
aggcccgcac cgatcgccct tcccaacagt tgcgcagcct gaatggcgaa tggcgattcc  1020
gttgcaatgg ctggcggtaa tattgttctg gatattacca gcaaggccga tagtttgagt  1080
tcttctactc aggcaagtga tgttattact aatcaaagaa gtattgcgac aacggttaat  1140
ttgcgtgatg gacagactct tttactcggt ggcctcactg attataaaaa cacttctcag  1200
gattctggc taccgttcct gtctaaaatc cctttaatcg gcctcctgtt tagctcccgc   1260
tctgattcta acgaggaaag cacgttatac gtgctcgtca aagcaaccat agtacgcgcc  1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg gctcccttta gggttccgat ttagtgcttt  1500
acggcacctc gaccccaaaa aacttgatta gggtgatggt tcacgtagtg ggccatcgcc  1560
ctgatagacg gttttttcgcc ctttgacgtt ggagtccacg ttctttaata gtggactctt  1620
gttccaaact ggaacaacac tcaaccctat ctcggtctat tcttttgatt tataagggat  1680
tttgccgatt tcggcctatt ggttaaaaaa tgagctgatt taacaaaaat ttaacgcgaa  1740
ttttaacaaa atattaacgt ttacaattta aatatttgct tatacaatct tcctgttttt  1800
ggggcttttc tgattatcaa ccggggtaca tatgattgac atgctagttt tacgattacc  1860
gttcatcgat tctcttgttt gctccagact ctcaggcaat gacctgatag cctttgtaga  1920
gacctctcaa aaatagctac cctctccggc atgaattat cagctagaac ggttgaatat   1980
catattgatg gtgatttgac tgtctccggc ctttctcacc cgtttgaatc tttacctaca  2040
cattactcag gcattgcatt taaaatatat gagggttcta aaaatttttta tccttgcgtt  2100
gaaataaagg cttctcccgc aaaagtatta cagggtcata atgtttttgg tacaaccgat  2160
ttagctttat gctctgaggc tttattgctt aattttgcta attctttgcc ttgcctgtat  2220
gatttattgg atgttggaat tcctgatgcg gtattttctc cttacgcatc tgtgcggtat  2280
ttcacaccgc atatggtgca ctctcagtac aatctgctct gatgccgcat agttaagcca  2340
gccccgacac ccgccaacac ccgctgacgc gccctgacgg gcttgtctgc tcccggcatc  2400
cgcttacaga caagctgtga ccgtctccgg gagctgcatg tgtcagaggt tttcaccgtc  2460
atcaccgaaa cgcgcgagac gaaagggcct cgtgatacgc ctatttttat aggttaatgt  2520
catgataata atggtttctt agacgtcagg tggcactttt cggggaaatg tgcgcggaac  2580
ccctatttgt ttatttttct aaatacattc aaatatgtat ccgctcatga caataacc     2640
ctgataaatg cttcaataat attgaaaaag gaagagtatg agtattcaac atttccgtgt  2700
cgcccttatt cccttttttg cggcattttg ccttcctgtt tttgctcacc cagaaacgct  2760
ggtgaaagta aaagatgctg aagatcagtt gggtgcacga gtgggttaca tcgaactgga  2820
tctcaacagc ggtaagatcc ttgagagttt tcgccccgaa gaacgttttc caatgatgag  2880
cacttttaaa gttctgctat gtggcgcggt attatcccgt attgacgccg ggcaagagca  2940
actcggtcgc cgcatacact attctcagaa tgacttggtt gagtactcac cagtcacaga  3000
aaagcatctt acggatggca tgacagtaag agaattatgc agtgctgcca taaccatgag  3060
tgataacact gcggccaact tacttctgac aacgatcgga ggaccgaagg agctaaccgc  3120
ttttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
gcgcaaacta ttaactggcg aactacttac tctagcttcc cggcaacaat taatagactg  3300
gatggaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctacacg acggggagtc aggcaactat  3480
ggatgaacga aatagacaga tcgctgagat aggtgcctca ctgattaagc attggtaact  3540
gtcagaccaa gtttactcat atatacttta gattgattta aaacttcatt tttaatttaa  3600
aaggatctag gtgaagatcc tttttgataa tctcatgacc aaaatccctt aacgtgagtt  3660
ttcgttccac tgagcgtcag accccgtaga aaagatcaaa ggatcttctt gagatccttt  3720
```

-continued

```
ttttctgcgc gtaatctgct gcttgcaaac aaaaaaacca ccgctaccag cggtggtttg    3780
tttgccggat caagagctac caactctttt tccgaaggta actggcttca gcagagcgca    3840
gataccaaat actgtccttc tagtgtagcc gtagttaggc caccacttca agaactctgt    3900
agcaccgcct acatacctcg ctctgctaat cctgttacca gtggctgctg ccagtggcga    3960
taagtcgtgt cttaccgggt tggactcaag acgatagtta ccggataagg cgcagcggtc    4020
gggctgaacg gggggttcgt gcacacagcc cagcttggag cgaacgacct cacccgaact    4080
gagataccta cagcgtgagc tatgagaaag cgccacgctt cccgaaggga gaaaggcgga    4140
caggtatccg gtaagcggca gggtcggaac aggagagcgc acgagggagc ttccagggggg   4200
aaacgcctgg tatctttata gtcctgtcgg gtttcgccac ctctgacttg agcgtcgatt    4260
tttgtgatgc tcgtcagggg ggcggagcct atggaaaaac gccagcaacg cggccttttt    4320
acggttcctg gccttttgct ggccttttgc tcacatgttc tttcctgcgt tatcccctga    4380
ttctgtggat aaccgtatta ccgcctttga gtgagctgat accgctcgcc gcagccgaac    4440
gaccgagcgc agcgagtcag tgagcgagga agcggaagag cgcccaatac gcaaaccgcc    4500
tctccccgcg cgttggccga ttcattaatg cagcagctgc gcgctcgctc gctcactgag    4560
gccgcccggg caaagcccgg gcgtcgggcg acctttggtc gcccggcctc agtgagcgag    4620
cgagcgcgca gagagggagt ggccaactcc atcactaggg gttccttgta gttaatgatt    4680
aacccgccat gctacttatc tacgtagcca tgctctagga cattgattat tgactagtgg    4740
agttccgcgt tacataactt acggtaaatg gcccgcctgg ctgaccgccc aacgacccc    4800
gcccattgac gtcaataatg acgtatgttc ccatagtaac gccaataggg actttccatt    4860
gacgtcaatg ggtggagtat ttacggtaaa ctgcccactt ggcagtacat caagtgtatc    4920
atatgccaag tacgccccct attgacgtca atgacggtaa atggcccgcc tggcattatg    4980
cccagtacat gaccttatgg gactttccta cttggcagta catctacgta ttagtcatcg    5040
ctattaccat ggtcgaggtg agccccacgt tctgcttcac tctccccatc tccccccct    5100
ccccaccccc aattttgtat ttatttattt tttaattatt ttgtgcagcg atggggggcgg   5160
ggggggggggg gggcgcgcgc caggcggggc ggggcggggc gaggggcggg gcggggcgag    5220
gcggagaggt gcggcggcag ccaatcagag cggcgcgctc cgaaagtttc cttttatggc    5280
gaggcggcgg cggcggcggc cctataaaaa gcgaagcgcg cggcgggcgg gagtcgctgc    5340
gcgctgcctt cgccccgtgc cccgctccgc cgccgcctcg cgccgcccgc cccggctctg    5400
actgaccgcg ttactaaaac aggtaagtcc ggcctccgcg ccgggttttg gcgcctcccg    5460
cgggcgcccc cctcctcacg gcgagcgctg ccacgtcaga cgaagggcgc agcgagcgtc    5520
ctgatccttc cgcccggacg ctcaggacag cggcccgctg ctcataagac tcggccttag    5580
aaccccagta tcagcagaag gacattttag gacgggactt gggtgactct agggcactgg    5640
ttttctttcc agagagcgga acaggcgagg aaaagtagtc ccttctcggc gattctgcgg    5700
agggatctcc gtggggcggt gaacgccgat gatgcctcta ctaaccatgt tcatgttttc    5760
ttttttttttc tacaggtcct gggtgacgaa cagggtaccg ccaccatgtc caccggctct    5820
cgcacaagcc tgctgctggc tttcggactg ctgtgcctgc cttggctcca ggagggctcc    5880
gccgctagca tcgataccgt cgctatgtgc tggaggcttg ctgaaggctg tatgctgtca    5940
ctcaccttttg tgcagaagac gttttggcct ctgactgacg tcttctgcaa aggtgagtga    6000
caggacacaa ggcctgttac tagcactcac atggaacaaa tggcctctag cctggaggct    6060
tgctgaaggc tgtatgctgg ttcttagcct atctcaagta gcgttttggc ctctgactga    6120
cgctacttga gaggctaaga cacaggacac aaggcctgtt actagcactc acatggaaca    6180
aatggcctct agcctggagg cttgctgaag gctgtatgct ggtctatgtc taaattccag    6240
cagcgttttg gcctctgact gacgctgctg gaatagacat gacacaggac acaaggcctg    6300
ttactagcac tcacatggaa caaatggcct ctctagaat                          6339
```

```
SEQ ID NO: 11          moltype = DNA   length = 6341
FEATURE                Location/Qualifiers
source                 1..6341
                       mol_type = other DNA
                       organism = synthetic construct
SEQUENCE: 11
aatcaacctc tggattacaa aatttgtgaa agattgactg gtattcttaa ctatgttgct    60
cctttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aacccccact    240
ggttggggca ttgccaccac ctgtcagctc ctttccggga ctttcgcttt ccccctccct    300
attgccacgg cggaactcat cgccgcctgc cttgcccgct gctggacagg ggctcggctg    360
ttgggcactg acaattccgt ggtgttgtcg gggaaatcat cgtcctttcc ttggctgctc    420
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc taagcttatc    600
gataccgtcg atctaact tgtttattgc agcttataat ggttacaaat aaagcaatag    660
catcacaaat ttcacaaata aagcatttt ttcactgcat tctagttgtg gtttgtccaa    720
actcatcaat gtatcttatc atgtctggat ctcgacctcg agagactcag tcgactacgtag  780
ataagtagca tggcgggtta atcattaact acaaggaacc cctagtgatg agttggcca    840
ctccctctct gcgcgctcgc tcgctcactg aggccgggcg accaaaggtc gcccgacgcc    900
cgggctttgc ccgggcggcc tcagtgagcg agcgagcgcg cagctggcgt aatagcgaag    960
aggcccgcac cgatcgccct tcccaacagt tgcgcagcct gaatggcgaa tggcgattcc    1020
gttgcaatgg ctggcggtaa tattgttctg gatattacca caaggccga tagtttgagt    1080
tcttctactc aggcaagtga tgttattact aatcaaagaa gtattgcgac aacggttaat    1140
ttgcgtgatg gacagactct tttactcggt ggcctcactg attataaaaa cacttctcag    1200
gattctggct taccgttcct gtctaaaatc ccttttaatcg gcctcctgtt tagctcccgc    1260
tctgattcta acgaggaaag cacgttatac gtgctcgtca aagcaaccat agtacgcgc    1320
ctgtagcggc gcattaagcg cggcgggtgt ggtggttacg cgcagcgtga cgctacact    1380
tgccagcgcc ctagcgcccg ctcctttcgc tttcttccct tcctttctcg ccacgttcgc    1440
cggctttccc cgtcaagctc taaatcgggg ctccctttta gggttccgat ttagtgcttt    1500
acggcacctc gaccccaaaa aacttgatta gggtgatggt tcacgtagtg gccatcgcc    1560
ctgatagacg gtttttcgcc ctttgacgtt ggagtccacg ttctttaata gtggactctt    1620
gttccaaact ggaacaacac tcaaccctat ctcggtctat tcttttgatt tataagggat    1680
```

-continued

```
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt taaaatatat gagggttcta aaaattttta tccttgcgtt   2100
gaaataaagg cttctcccgc aaaagtatta cagggtcata atgttttttgg tacaaccgat   2160
ttagctttat gctctgaggc tttattgctt aattttgcta attctttgcc ttgcctgtat   2220
gatttattgg atgttggaat tcctgatgcg gtatttttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcactttt cggggaaatg tgcgcggaac   2580
ccctatttgt ttatttttct aaatacattc aaatatgtat ccgctcatga gacaataacc   2640
ctgataaatg cttcaataat attgaaaaag gaagagtatg agtattcaac atttccgtgt   2700
cgcccttatt cccttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
ttttttgcac aacatggggg atcatgtaac tcgccttgat cgttgggaac cggagctgaa   3180
tgaagccata ccaaacgacg agcgtgacac cacgatgcct gtagcaatgg caacaacgt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagatacccta cagcgtgagc tatgagaaag cgccacgctt cccgaaggga aaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggccttttt   4320
acggttcctg gccttttgct ggccttttgc tcacatgttc tttcctgcgt tatccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcct   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagaggagt ggccaactcc atcactaggg gttccttgta gttaatgatt   4680
aacccgccat gctacttatc tacgtagcca tgctctagag cattgattat tgactagttg   4740
agttccgcgt tacataactt acggtaaatg gcccgcctgg ctgaccgccc aacgacccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tcccccccct   5100
ccccacccc aattttgtat ttatttattt tttaattatt ttgtgcagcg atggggcgg   5160
ggggggggg gggcgcgcgc caggcggggc ggggcggggc gaggggcggg gcggggcgag   5220
gcggagaggt gcggcgcag ccaatcagag cggcgcgctc cgaaagtttc ctttatggcg   5280
gaggcggcag cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg gcgagcgctg ccacgtcaga cgaagggcgc agcgagcgtc   5520
ctgatccttc cgcccggacg ctcaggacag cggcccgctg ctcataagac tcggccttag   5580
aaccccagta tcagcagaag gacattttag gacgggactt gggtgactct agggcactgg   5640
ttttctttcc agagagcgga acaggcgagg aaaagtagtc ccttctcggc gattctgcgg   5700
agggatctcc gtgggcggt gaacgccgat gatgcctcta ctaaccatgt tcatgttttc   5760
tttttttttc tacaggtcct gggtgacgaa cagggtaccg ccaccatgtc caccggctct   5820
cgcacaagcc tgctgctggc tttcggactc ctgtgcctgc cttggctcca ggagggctcc   5880
gccgctagca tcgataccgt cgctatgtgc tggaggcttg ctgaaggctg tatgctgctc   5940
acttgaattg cttaccgctc cgttttggcc tctgactgac ggagcggtaa gattcaagtg   6000
agcaggacac aaggcctgtt actagcactc acatggaaca aatggcctct agcctggagg   6060
cttgctgaag gctgtatgct gtgtctgatc ctatctcaag tagcgttttg gcctctgact   6120
gacgctactt gagaggctaa gacacaggac acaaggcctg ttactagcac tcacatggaa   6180
caaatggcct ctagcctgga ggcttgctga aggctgtatg ctgatgtttc gggaaacag   6240
tgactcgttt tggcctctga ctgacgattc actgtcccgg aaacatcagg acacaaggcc   6300
tgttactagc actcacatgg aacaaatggc ctctctagaa t               6341
```

COMPOSITION FOR REGULATING PRODUCTION OF INTERFERING RIBONUCLEIC ACID

CROSS REFERENCE TO RELATED APPLICATION

The present application is a continuation of U.S. patent application Ser. No. 18/518,177 filed Nov. 22, 2023, entitled "COMPOSITION FOR REGULATING PRODUCTION OF INTERFERING RIBONUCLEIC ACID" currently pending, the entirety of which are incorporated herein by reference.

SEQUENCE LISTING

This application contains a Sequence Listing electronically submitted via Patent Center to the United States Patent and Trademark Office as an XML Document file entitled "A8149361US—Sequence Listing.xml" created on 2023 Nov. 17 and having a size of 49,999 bytes. The information contained in the Sequence Listing is incorporated by reference herein.

TECHNICAL FIELD

The present disclosure generally relates to compositions for regulating production of interfering ribonucleic acid (RNA). In particular, the present disclosure relates to compositions for regulating gene expression and therefore, the production of interfering RNA, that will suppress checkpoint molecule overexpression or mis-expression.

BACKGROUND

Bioactive molecules, including checkpoint molecules, are necessary for the homeostatic control of biological systems.

When bioactive molecules are over-expressed or mis-expressed, homeostasis is lost, and disease is often the result.

As such, it may be desirable to establish therapies, treatments and/or interventions that address when homeostasis and regulation of bioactive molecules is lost to prevent or treat the resulting disease.

SUMMARY

Some embodiments of the present disclosure relate to one or more compositions that upregulate the production of one or more sequences of micro interfering ribonucleic acid (miRNA). The sequences of miRNA may be complementary to a sequence of target messenger RNA (mRNA) that encodes for translation of a target biomolecule and the miRNA can cause the target mRNA to be degraded or inactivated, thereby causing a decrease in bioavailability of the target biomolecule because it is degraded or inactivated by the miRNA, thereby decreasing the bioavailability of the target biomolecule within a subject that is administered the one or more compositions. In some embodiments of the present disclosure, the target biomolecule is an immune checkpoint molecule. In some embodiments of the present disclosure, the target biomolecule is an immune checkpoint molecule such as PD-1. In some embodiments of the present disclosure, the target biomolecule is an immune checkpoint molecule such as PD-L1. In some embodiments of the present disclosure, the target biomolecule is an immune checkpoint molecule such as PD-L2. In some embodiments of the present disclosure, the target biomolecule is an immune checkpoint molecule such as CTLA4. In some embodiments of the present disclosure, the target biomolecule is an immune checkpoint molecule such as IDO1. In some embodiments of the present disclosure, the target biomolecule participates, directly or indirectly, in one or more immune responses. For example, the target biomolecule may be an immune checkpoint molecule that is a protein, a protein-protein complex—such as a receptor ligand pair—or other type of biomolecule that directly or indirectly inhibits an immune response or that directly or indirectly stimulates an immune response.

In some embodiments of the present disclosure the compositions comprise a plasmid of deoxyribonucleic acid (DNA) that includes one or more insert sequences of nucleic acids that encode for the production of miRNA and a backbone sequence of nucleic acids that facilitates introduction of the one or more insert sequences into one or more of a subject's cells where it is expressed and/or replicated. Expression of the one or more insert sequences by one or more cells of the subject results in an increased production of the miRNA and, therefore, decreased translation or production of the target biomolecule by one or more of the subject's cells.

Some embodiments of the present disclosure relate to compositions that upregulate the production of miRNA that degrades, or causes degradation of, or inactivates or causes the inactivation of, the target mRNA of the target biomolecule.

Some embodiments of the present disclosure relate to a recombinant plasmid (RP). In some embodiments of the present disclosure, the RP comprises a nucleotide sequence of SEQ ID NO. 1 and SEQ ID NO. 2. The RP comprises a nucleotide sequence encoding one or more nucleotide sequences encoding a miRNA sequence that targets mRNA of PD-1.

Some embodiments of the present disclosure relate to a recombinant plasmid. In some embodiments of the present disclosure, the RP comprises a nucleotide sequence of SEQ ID NO. 1 and SEQ ID NO. 3. The RP comprises a nucleotide sequence encoding one or more nucleotide sequences encoding a miRNA sequence that targets mRNA of PD-L1.

Some embodiments of the present disclosure relate to a recombinant plasmid. In some embodiments of the present disclosure, the RP comprises a nucleotide sequence of SEQ ID NO. 1 and SEQ ID NO. 4. The RP comprises a nucleotide sequence encoding one or more nucleotide sequences encoding a miRNA sequence that targets mRNA of PD-L2.

Some embodiments of the present disclosure relate to a recombinant plasmid. In some embodiments of the present disclosure, the RP comprises a nucleotide sequence of SEQ ID NO. 1 and SEQ ID NO. 5. The RP comprises a nucleotide sequence encoding one or more nucleotide sequences encoding a miRNA sequence that targets mRNA of CTLA4.

Some embodiments of the present disclosure relate to a recombinant plasmid. In some embodiments of the present disclosure, the RP comprises a nucleotide sequence of SEQ ID NO. 1 and SEQ ID NO. 6. The RP comprises a nucleotide sequence encoding one or more nucleotide sequences encoding a miRNA sequence that targets mRNA of IDO1.

Some embodiments of the present disclosure relate to a method of making a composition/target cell complex. The method comprising a step of administering a RP comprising SEQ ID NO. 1 and one of SEQ ID NO. 2, SEQ ID NO. 3, SEQ ID NO. 4, SEQ ID NO. 5, or SEQ ID NO. 6, to a target cell for forming the composition/target cell complex, wherein the composition/target cell complex causes the target cell to increase production of one or more sequences of miRNA that decreases production of a target biomolecule.

Embodiments of the present disclosure relate to at least one approach for inducing endogenous production of one or more sequences of miRNA that target and silence mRNA of a target biomolecule, for example PD-1. A first approach utilizes gene vectors containing nucleotide sequences for increasing the endogenous production of one or more sequences of miRNA, which are complete or partial sequences and/or combinations thereof, that target and silence the mRNA of PD-1, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example PD-L1. A first approach utilizes gene vectors containing nucleotide sequences for increasing the endogenous production of one or more sequences of miRNA, which are complete or partial sequences and/or combinations thereof, that target and silence the mRNA of PD-L1, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example PD-L2. A first approach utilizes gene vectors containing nucleotide sequences for increasing the endogenous production of one or more sequences of miRNA, which are complete or partial sequences and/or combinations thereof, that target and silence the mRNA of PD-L2, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example CTLA4. A first approach utilizes gene vectors containing nucleotide sequences for increasing the endogenous production of one or more sequences of miRNA, which are complete or partial sequences and/or combinations thereof, that target and silence the mRNA of CTLA4, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example IDO1. A first approach utilizes gene vectors containing nucleotide sequences for increasing the endogenous production of one or more sequences of miRNA, which are complete or partial sequences and/or combinations thereof, that target and silence the mRNA of IDO1, which can be administered to a subject to increase the subject's production of one or more sequences of the miRNA.

DETAILED DESCRIPTION

Unless defined otherwise, all technical and scientific terms used therein have the meanings that would be commonly understood by one of skill in the art in the context of the present description. Although any methods and materials similar or equivalent to those described therein can also be used in the practice or testing of the present disclosure, the preferred methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "ameliorate" refers to improve and/or to make better and/or to make more satisfactory.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the one or more target cells' production of one or more proteins, and/or any post-translational modifications of one or more proteins.

As used therein, the term "composition" refers to a substance that, when administered to a subject, causes one or more chemical reactions and/or one or more physical reactions and/or one or more physiological reactions and/or one or more immunological reactions in the subject. In some embodiments of the present disclosure, the composition is a plasmid vector.

As used therein, the term "endogenous" refers to the production and/or modification of a molecule that originates within a subject.

As used therein, the term "exogenous" refers to a molecule that is within a subject but that did not originate within the subject. As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target biomolecule" refers to a checkpoint molecule that is found within a subject. A biomolecule may be endogenous or exogenous to a subject and when bioavailable the biomolecule may inhibit or stimulate an immune process within the subject.

As used therein, the term "target cell" refers to one or more cells and/or cell types that are deleteriously affected, either directly or indirectly, by a dysregulated biomolecule. The term "target cell" also refers to cells that are not deleteriously affected but that are the cells in which it is desired that the composition interacts.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, a composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus vector.

In some embodiments of the present disclosure, the insert comprises one or more nucleotide sequences that encode for production of at least one sequence of miRNA that decreases the production of target biomolecules. The miRNA may, directly or indirectly, bind to and degrade the target mRNA or otherwise inactivate the target mRNA so that less or none of the target-biomolecule protein is produced.

In some embodiments of the present disclosure, the target biomolecule is PD-1.

In some embodiments of the present disclosure, the target biomolecule is PD-L1.

In some embodiments of the present disclosure, the target biomolecule is PD-L2.

In some embodiments of the present disclosure, the target biomolecule is CTLA4.

In some embodiments of the present disclosure, the target biomolecule is IDO1.

In some embodiments of the present disclosure, the insert comprises one or more nucleotide sequences that each encode one or more miRNA sequences that may be complementary to and degrade, or cause degradation of, mRNA of the target biomolecule.

Some embodiments of the present disclosure relate to a composition that can be administered to a subject with a condition that results, directly or indirectly, from the production of a dysregulated biomolecule. When a therapeutically effective amount of the composition is administered to the subject, the subject may change production and/or functionality of one or more biomolecules.

In some embodiments of the present disclosure, the subject may respond to receiving the therapeutic amount of the composition by changing production and/or functionality of one or more intermediary molecules by changing production of one or more DNA sequences, one or more RNA sequences, and/or one or more proteins that regulate the levels and/or functionality of the one or more intermediary molecules. The one or more intermediary molecules regulate the subject's levels and/or functionality of the one or more biomolecules.

In some embodiments of the present disclosure, administering a therapeutic amount of the composition to a subject upregulates the production, functionality or both one or more sequences of miRNA that each target the mRNA of one or more target biomolecules. In some embodiments of the present disclosure, there are one, two, three, four, five, or six miRNA sequences that each are complementary to and degrade, or cause degradation of, one biomolecule, such as PD-1, PD-L1, PD-L2, CTLA4, or IDO1. In some embodiments of the present disclosure, the composition may comprise multiple copies of the same nucleotide sequence of miRNA.

In some embodiments of the present disclosure, the composition is an RP that may be used for gene therapy. The gene therapy is useful for increasing the subject's endogenous production of one or more sequences of miRNA that target the mRNA of a target biomolecule. For example, the RP can contain one or more nucleotide sequences that cause increased production of one or more nucleotide sequences that cause an increased production of one or more miRNA sequences that are each complementary to and degrade, or cause degradation of, or inactivate, or cause inactivation of, one biomolecule, such as PD-1, PD-L1, PD-L2, CTLA4, or IDO1.

In some embodiments of the present disclosure, the delivery vehicle of the RP used for gene therapy may be a virus that can be enveloped, or not (unenveloped), replication effective or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus *Dependoparvovirus*. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle of the RP used for gene therapy may be a protein coat.

In some embodiments of the present disclosure, the delivery vehicle of the RP used for gene therapy may be a lipid vesicle.

The embodiments of the present disclosure also relate to administering a therapeutically effective amount of the composition. In some embodiments of the present disclosure, the therapeutically effective amount of the composition that is administered to a patient is between about 10 and about $1\times10^{16}$ TCID$_{50}$/kg (50% tissue culture infective dose per kilogram of the patient's body mass. In some embodiments of the present disclosure, the therapeutically effective amount of the composition that is administered to the patient is about $1\times10^{13}$ TCID$_{50}$/kg. In some embodiments of the present disclosure, the therapeutically effective amount of the composition that is administered to a patient is measured in TPC/kg (total particle count of the composition per kilogram of the patient's body mass). In some embodiments the therapeutically effective amount of the composition is between about 10 and about $1\times10^{16}$ TCP/kg.

Some embodiments of the present disclosure relate to an adenovirus associated virus (AAV) genome consisting of a RP that when operable inside a target cell will cause the target cell to produce a miRNA sequence that downregulates production of a biomolecule, with examples being PD-1, PD-L1, PD-L2, CTLA4, or IDO1. The RP is comprised of AAV2 inverted terminal repeats (ITRs), a composite CASI promoter, a human growth hormone (HGH) signal peptide followed by a miRNA expression cassette containing up to six different miRNAs targeting PD-1, PD-L1. PD-L2. CTLA4, or IDO1, followed by a Woodchuck Hepatitis Virus post-transcriptional regulatory element (WPRE) and an SV40 polyA signal.

SEQ ID NO. 1 (backbone sequence No. 1):
5' aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaacccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtccttcggccctc aatccagcggaccttccttcccgcggcctgctgccggctctgcgggcctcttccgcgtcttcgccttcgccctcagacgagtcggatctccctttt gggccgcctccccgcctaagcttatcgataccgtcgagatctaacttgtttattgcagcttataatggttacaaataaagcaatagcatcacaaa tttcacaaataaagcattttttcactgcattctagttgtggtttgtccaaactcatcaatgtatcttatcatgtctggatctcgacctcgactagagc atggctacgtagataagtagcatggcgggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggtacgcgcagcgtgaccgctacacttgccagcgccctagcgcccgctcctttcgctttctt cccttcctttctcgccacgttcgccggctttccccgtcaagctctaaatcggggggctccctttagggttccgatttagtgctttacggcacctcga ccccaaaaaacttgattagggtgatggttcacgtagtgggccatcgcccctgatagacggtttttcgcccctttgacgttggagtccacgttcttta atagtggactcttgttccaaactggaacaacactcaaccctatctcggtctattcttttgatttataagggattttgccgatttcggcctattggtaa aaaatgagctgatttaacaaaaatttaacgcgaattttaacaaaatattaacgtttacaatttaaatatttgcttatacaatcttcctgttttttggggct tttctgattatcaaccggggtacatatgattgacatgctagtttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcacccgtttgaatctttacctacacattactcaggcattgcatttaaaatatatgagggttctaaaaattttttatccttgcgttg aaataaaggcttctcccgcaaaagtattacagggtcataatgttttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttattttttctaaatacattcaaatatgtatccgctcatgagacaataaccctgataaatgcttcaataatattgaaaaaggaagagt atgagtattcaacatttccgtgtcgcccttattccctttttttgcggcattttgccttcctgttttttgctcacccagaaacgctggtgaaagtaaaagat gctgaagatcagttgggtgcacgagtgggttacatcgaactggatctcaacagcggtaagatccttgagagttttcgccccgaagaacgttttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagacccgtagaaaagatcaaaggatcttct tgagatcctttttttctgcgcgtaatctgctgcttgcaaacaaaaaaaccaccgctaccagcggtggtttgtttgccggatcaagagctaccaac tcttttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccaggggggaaacgcctggtatctttatagtcctgtcgggtttcgccacctctgacttgagcgtcgat ttttgtgatgctcgtcaggggggcggagcctatgaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactaggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc ccccccctccccaccccaattttgtatttatttattttttaattattttgtgcagcgatggggcggggggggggggggcgcgcgccaggc ggggcggggcggggcgaggggcggggcggggcgaggcggagaggtgcggcggcagccaatcagagcggcgcgctccgaaagttt ccttttatggcgaggcggcggcggcggcggcccctataaaaagcgaagcgcgcgggggggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaacccagtatcagcagaaggacatttttaggacgggacttgggt gactctagggcactggttttctttccagagagcggaacaggcgaggaaaagtagtcccttctcggcgattctgcggagggatctccgtggg gcggtgaacgccgatgatgcctctactaaccatgttcatgttttcttttttttttctacaggtcctgggtgacgaacagggtaccgccaccatggc caccggctctcgcacaagcctgctgctggctttcggactgctgtgcctgcccttggctccaggagggctccgcc 3'

SEQ ID NO. 2 (miRNA expression cassette No. 2-PD-1):
5' gctagcatcgataccgtcgctatgtgctggaggcttgctgaaggctgtatgctgtacctaagaactgcatcctggccgttttggcctctgactg acggccaggatggttcttaggtacaggacacaaggcctgttactagcactcacatggaacaaatggcctctagcctggaggcttgctgaag gctgtatgctgtcgtaaagccaataggttagtcccgttttggcctctgactgacgggactaaccttggctttacgacaggacacaaggcctgtt actagcactcacatggaacaaatggcctctagcctggaggcttgctgaaggctgtatgctgagagagaccgcaaattaccggacggttttg -continued gcctctgactgaccgtcctgtaatgcggtctctctcaggacacaaggcctgttactagcactcacatggaacaaatggcctctctagaat 3'

SEQ ID NO. 3 (miRNA expression cassette No. 3-PD-L1):
5' gctagcatcgataccgtcgctatgtgctggaggcttgctgaaggctgtatgctgagagacttacttgtagatgctgcgttttggcctctgactga cgcagcatctaagtaagtctctcaggacacaaggcctgttactagcactcacatggaacaaatggcctctagcctggaggcttgctgaaggc tgtatgctgactatttcatcatactctcacccgttttggcctctgactgacgggtgagagtgatgaaatagtcaggacacaaggcctgttactag cactcacatggaacaaatggcctctagcctggaggcttgctgaaggctgtatgctgatatgaatgacaatcacagccgagttttggcctctga ctgacgtggctgtgagtcattcatatcaggacacaaggcctgttactagcactcacatggaacaaatggcctctctagaat 3'

SEQ ID NO. 4 (miRNA expression cassette No. 4-PD-L2):
5' gctagcatcgataccgtcgctatgtgctggaggcttgctgaaggctgtatgctgacaatcaacattggcagtagctcgttttggcctctgactg acgagctactgcatgttgattgtcaggacacaaggcctgttactagcactcacatggaacaaatggcctctagcctggaggcttgctgaagg ctgtatgctgaataagcctttatccatagtcccgttttggcctctgactgacgggactatggaaaggcttattcaggacacaaggcctgttacta gcactcacatggaacaaatggcctctagcctggaggcttgctgaaggctgtatgctgacaactgtctcaaattactgctcgttttggcctctga ctgacgagcagtaatgagacagttgtcaggacacaaggcctgttactagcactcacatggaacaaatggcctctctagaat 3'

SEQ ID NO. 5 (miRNA expression cassette No. 5-CTLA4):
5' gctagcatcgataccgtcgctatgtgctggaggcttgctgaaggctgtatgctgtcactcacctttgtgcagaagacgttttggcctctgactg acgtcttctgcaaaggtgagtgacaggacacaaggcctgttactagcactcacatggaacaaatggcctctagcctggaggcttgctgaag gctgtatgctggttcttagcctatctcaagtagcgttttggcctctgactgacgctacttgagaggctaagacacaggacacaaggcctgttac tagcactcacatggaacaaatggcctctagcctggaggcttgctgaaggctgtatgctggtctatgtctaaattccagcagcgttttggcctct gactgacgctgctggaatagacatgacacaggacacaaggcctgttactagcactcacatggaacaaatggcctctctagaat 3'

SEQ ID NO. 6 (miRNA expression cassette No. 6-IDO1):
5' gctagcatcgataccgtcgctatgtgctggaggcttgctgaaggctgtatgctgctcacttgaattgcttaccgctccgttttggcctctgactg acggagcggtaagattcaagtgagcaggacacaaggcctgttactagcactcacatggaacaaatggcctctagcctggaggcttgctga aggctgtatgctgtgtctgatcctatctcaagtagcgttttggcctctgactgacgctacttgagaggctaagacacaggacacaaggcctgtt actagcactcacatggaacaaatggcctctagcctggaggcttgctgaaggctgtatgctgatgtttccgggaaacagtgactcgttttggcc tctgactgacgattcactgtcccgggaaacatcaggacacaaggcctgttactagcactcacatggaacaaatggcctctctagaat 3'

SEQ ID NO: 7 = SEQ ID NO: 1 + SEQ ID NO: 2
5' aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaacccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcgggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatcttatcatgtctggatctgacctcgactagagc atggctacgtagataagtagcatgggggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcggggggctcccctttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaatttttaacaaaatattaacgtttacaattttaaatatttgcttatacaatcttcctgtttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcacccgtttgaatctttacctacacattactcaggcattgcatttaaaatatatgagggttctaaaaattttttatccttgcgttg aaataaaggcttctcccgcaaaagtattacaggtgtcataatgttttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacaccgccaacaccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctattttatatggttaatgtcatgataataatggtttcttagacgtcaggtggcacttttcggggaaatgtgcgcggaa cccctatttgtttattttttctaaatacattcaaatatgtatccgctcatgagacaataaccctgataaatgcttcaataatattgaaaaaggaagagt atgagtattcaacatttccgtgtcgcccttattccctttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagacccccgtagaaaagatcaaaggatcttct tgagatcctttttttctgcgcgtaatctgctgcttgcaaacaaaaaaaccaccgctaccagcggtggtttgtttgccggatcaagagctaccaac tcttttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccagggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactaggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc cccccctccccaccccaattttgtatttatttattttttaattattttgtgcagcgatggggcggggggggggggggcgcgcgccaggc ggggcggggcggggcgaggggcggggcggggcgaggcggagaggtgcggcggcagccaatcagagcggcgcgctccgaaagttt cctttttatggcgaggcggcggcggcggcggcgggccctataaaaagcgaagcgcgcggggggggagtcgctgcgcgctgccttcgcccc gtgccccgctccgccgccgcctcgcgccgcccgccccggctctgactgaccgcgttactaaaacaggtaagtccggcctccgcgccggg -continued ttttggcgcctcccgcgggcgccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt gactctagggcactggttttctttccagagagcggaacaggcgaggaaaagtagtcccttctcggcgattctgcggagggatctccgtggg gcggtgaacgccgatgatgcctctactaaccatgttcatgtttttcttttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgtacctaagaactgcatcctggccgttttggcctctgactgacgccaggatggttctt aggtacaggacacaaggcctgttactagcactcacatggaacaaatggcctctagcctggaggcttgctgaaggctgtatgctgtcgtaaag ccaataggttagtcccgttttggcctctgactgacgggactaaccttggctttacgacaggacacaaggcctgttactagcactcacatggaa caaatggcctctagcctggaggcttgctgaaggctgtatgctgagagagaccgcaaattaccggacggttttggcctctgactgaccgtcct gtaatgcggtctctctcaggacacaaggcctgttactagcactcacatggaacaaatggcctctctagaat 3'

SEQ ID NO: 8 = SEQ ID NO: 1 + SEQ ID NO: 3
5' aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaaccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcgggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatcttatcatgtctggatctcgacctcgac tagagc atggctacgtagataagtagcatggcgggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcggggggctcccctttagggttccgatttagtgctttacggcacctcga ccccaaaaaacttgattagggtgatggttcacgtagtgggccatcgccctgatagacggtttttcgccctttgacgttggagtccacgttctttta atagtggactcttgttccaaactggaacaacactcaaccctatctcggtctattcttttgatttataagggattttgccgatttcggcctattggttaa aaaatgagctgatttaacaaaaatttaacgcgaattttaacaaaatattaacgtttacaatttaaatatttgcttatacaatcttcctgttttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcaccgtttgaatctttacctacacattactcaggcattgcatttaaaatatatgagggttctaaaaattttttatccttgcgttg aaataaaggcttctcccgcaaaagtattacagggtcataatgtttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttatttttctaaatacattcaaatatgtatccgctcatgagacaataaccctgataaatgcttcaataatattgaaaaaggaagagt atgagtattcaacatttccgtgtcgcccttattcccttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgctttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcattttaatttaaaaggatctaggtg aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggtttgtttgccggatcaagagctaccaac tctttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccaggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactaggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc cccccctccccaccccaattttgtatttatttattttttaattattttgtgcagcgatggggcggggggggggggggcgcgcgccaggc ggggcggggcggggcgaggggcggggcggggcgaggcggagaggtgcggcggcagccaatcagagcggcgcgctccgaaagttt cctttatggcgaggcggcggcggcggcggccctataaaaagcgaagcgcgcggcgggcgggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaacccagtatcagcagaaggacattttaggacgggacttgggt gactctagggcactggtttctcttccagagagcggaacaggcgaggaaaagtagtcccttctcggcgattctgcggagggatctccgtggg gcggtgaacgccgatgatgcctctactaaccatgttcatgtttttctttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgagagacttacttgtagatgctgcgttttggcctctgactgacgcagcatctaagtaagt ctctcaggacacaaggcctgttactagcactcacatggaacaaatggcctctagcctggaggcttgctgaaggctgtatgctgactattttcatc atactctcacccgttttggcctctgactgacgggtgagagtgatgaaatagtcaggacacaaggcctgttactagcactcacatggaacaaat ggcctctagcctggaggcttgctgaaggctgtatgctgatatgaatgacaatcacagccgagttttggcctctgactgacgtggctgtgagtc attcatatcaggacacaaggcctgttactagcactcacatggaacaaatggcctctctagaat 3'

SEQ ID NO: 9 = SEQ ID NO: 1 + SEQ ID NO: 4
5' aatcaacctctggattacaaaatttgtgaaagattgactggtattcttaactatgttgctccttttacgctatgtggatacgctgctttaatgcctttgt atcatgctattgcttcccgtatggctttcatttttctcctccttgtataaatcctggttgctgtctctttatgaggagttgtggcccgttgtcaggcaac -continued gtggcgtggtgtgcactgtgtgtttgctgacgcaaccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcgggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatccttatcatgtctggatctcgacctcgactagagc atggctacgtagataagtagcatggcgggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactctttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcggggctccctttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaattttaacaaaatattaacgtttacaatttaaatatttgcttatacaatcttcctgtttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcacccgtttgaatctttacctacacattactcaggcattgcatttaaaatatatgaggggttctaaaaatttttatccttgcgttg aaataaaggcttctcccgcaaaagtattacagggtcataatgtttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttattttttctaaatacattcaaatatgtatccgctcatgagacaataaccctgataaatgcttcaataatattgaaaaaggaagagt atgagtattcaacatttccgtgtcgcccttattcccttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagacccccgtagaaaagatcaaaggatcttct tgagatcctttttttctgcgcgtaatctgctgcttgcaaacaaaaaaaccaccgctaccagcggtggtttgtttgccggatcaagagctaccaac tcttttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac -continued gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccaggggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggcctttttgctggcctttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactagggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc cccccctccccacccccaattttgtatttatttattttttaattattttgtgcagcgatggggcggggggggggggggggcgcgcgccaggc ggggcggggcggggcgaggggcggggcggggcgaggcggagaggtgcggcggcagccaatcagagcggcgcgctccgaaagttt ccttttatggcgaggcggcggcggcggcggccctataaaaagcgaagcgcgcggcgggcgggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt gactctaggcactggtttctttccagagagcggaacaggcgaggaaaagtagtcccttctcggcgattctgcggagggatctccgtggg gcggtaacgccgatgatgcctctactaaccatgttcatgtttctttttttttctacaggtcctgggtgacgaacagggtaccgccaccatggc caccggctctcgcacaagcctgctgctggctttcggactgctgtgcctgcccttggctccaggagggctccgccgctagcatcgataccgtc gctatgtgctggaggcttgctgaaggctgtatgctgacaatcaacattggcagtagctcgtttttggcctctgactgacgagctactgcatgttg attgtcaggacacaaggcctgttactagcactcacatggaacaaatggcctctagcctggaggcttgctgaaggctgtatgctgaataagcct ttatccatagtcccgtttttggcctctgactgacgggactatggaaaggcttattcaggacacaaggcctgttactagcactcacatggaacaaa tggcctctagcctggaggcttgctgaaggctgtatgctgacaactgtctcaaattactgctcgtttttggcctctgactgacgagcagtaatgag acagttgtcaggacacaaggcctgttactagcactcacatggaacaaatggcctctctagaat 3'

SEQ ID NO: 10 = SEQ ID NO: 1 + SEQ ID NO: 5
5'aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaaccccactggttggggcattgccaccacctgtcagctcctttccgggactttcgctttccc cctccctattgccacggcggaactcatcgccgctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctccctt gggccgcctccccgcctaagcttatcgataccgtcgagatctaacttgtttattgcagcttataatggttacaaataaagcaatagcatcacaaa tttcacaataaagcatttttttcactgcattctagttgtggtttgtccaaactcatcaatgtatcttatcatgtctggatctcgacctcgactagagc atggctacgtagataagtagcatggcgggttaatcattaactacaaggaaccccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt -continued

```
agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcggggggctcccctttagggttccgatttagtgctttacggcacctcga ccccaaaaaacttgattagggtgatggttcacgtagtgggccatcgccctgatagacggttttttcgcccttttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaattttaacaaaatattaacgtttacaatttaaatatttgcttatacaatcttcctgttttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcacccgtttgaatctttacctacacattactcaggcattgcatttaaaatatatgaggggttctaaaaatttttatccttgcgttg aaataaaaggcttctcccgcaaaagtattacagggtcataatgttttttggtacaaccgatttagctttatgctctgaggctttattgcttaattttgcta attcttttgccttgcctgtatgatttattggatgttggaattcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttattttttctaaatacattcaaatatgtatccgctcatgagacaataaccctgataaatgcttcaataatattgaaaaaggaagagt atgagtattcaacatttccgtgtcgcccttattccctttttttgcggcattttgccttcctgttttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcactttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggtttgtttgccggatcaagagctaccaac tcttttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccaggggggaaacgcctggtatctttatagtcctgtcgggtttcgccacctctgacttgagcgtcgat ttttgtgatgctcgtcagggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactagggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc ccccccctccccaccccaattttgtatttatttattttttaattattttgtgcagcgatgggggcgggggggggggggggcgcgcgccaggc
``` ggggcggggcggggcgaggggcggggcggggcgaggcggagaggtgcggcggcagccaatcagagcggcgcgctccgaaagttt cctttttatggcgaggcggcggcggcggcggccctataaaaagcgaagcgcgcggggggggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt gactctagggcactggttttctttccagagagcggaacaggcgaggaaaagtagtcccttctcggcgattctgcggagggatctccgtggg gcggtgaacgccgatgatgcctctactaaccatgttcatgttttcttttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgtcactcacctttgtgcagaagacgttttggcctctgactgacgtcttctgcaaaggtga gtgacaggacacaaggcctgttactagcactcacatggaacaaatggcctctagcctggaggcttgctgaaggctgtatgctggttcttagc ctatctcaagtagcgttttggcctctgactgacgctacttgagaggctaagacacaggacacaaggcctgttactagcactcacatggaacaa atggcctctagcctggaggcttgctgaaggctgtatgctggtctatgtctaaattccagcagcgtttttggcctctgactgacgctgctggaata gacatgacacaggacacaaggcctgttactagcactcacatggaacaaatggcctctctagaat 3'

SEQ ID NO: 11 = SEQ ID NO: 1 + SEQ ID NO: 6
5'aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaacccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatcttatcatgtctggatctcgacctcgactagagc atggctacgtagataagtagcatggcgggttaatcattaactacaaggaaccccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcgggggctccctttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaattttaacaaaatattaacgtttacaatttaaatatttgcttatacaatcttcctgttttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcaccgtttgaatctttacctacacattactcaggcattgcatttaaaatatatgagggttctaaaaattttttatccttgcgttg aaataaaggcttctcccgcaaaagtattacagggtcataatgttttttggtacaaccgatttagctttatgctctgaggctttattgcttaattttgcta attctttgccttgcctgtatgatttattggatgttggaatcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttattttttctaaatacattcaaatatgtatccgctcatgagacaataaccctgataaatgcttcaataatattgaaaaaggaagagt atgagtattcaacatttccgtgtcgcccttattccctttttttgcggcattttgccttcctgtttttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgctttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccccccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcattttttaatttaaaaggatctaggtg aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggtttgtttgccggatcaagagctaccaac tcttttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccaggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggcctttttgctggcctttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactagggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgggtggagtatttacggtaaactgcccacttgg cagtacatcaagtgtatcatatgccaagtacgcccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc cccccctccccacccccaattttgtatttatttattttttaattattttgtgcagcgatggggcggggggggggggggggcgcgcgccaggc ggggcggggcggggcgaggggcggggcggggcgaggcggagaggtgcggcggcagccaatcagagcggcgcgctccgaaagttt ccttttatggcgaggcggcggcggcggcggccctataaaaagcgaagcgcgcggggggggagtcgctgcgcgctgccttcgcccc gtgccccgctccgccgccgcctcgcgccgccccgcccggctctgactgaccgcgttactaaaacaggtaagtccggcctccgcgccggg ttttggcgcctcccgcgggcgccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt gactctagggcactggttttctttccagagagcggaacaggcgaggaaaagtagtcccttctcggcgattctgcggagggatctccgtggg gcggtgaacgccgatgatgcctctactaaccatgttcatgttttcttttttttttctacaggtcctgggtgacgaacagggtaccgccaccatggc caccggctctcgcacaagcctgctgctggctttcggactgctgtgcctgccttggctccaggagggctccgcgcgctagcatcgataccgtc gctatgtgctggaggcttgctgaaggctgtatgctgctcacttgaattgcttaccgctccgttttggcctctgactgacggagcggtaagattca -continued agtgagcaggacacaaggcctgttactagcactcacatggaacaaatggcctctagcctggaggcttgctgaaggctgtatgctgtgtctga tcctatctcaagtagcgttttggcctctgactgacgctacttgagaggctaagacacaggacacaaggcctgttactagcactcacatggaac aaatggcctctagcctggaggcttgctgaaggctgtatgctgatgtttccgggaaacagtgactcgttttggcctctgactgacgattcactgt cccggaaacatcaggacacaaggcctgttactagcactcacatggaacaaatggcctctctagaat 3'

As will be appreciated by those skilled in the art, because the recombinant plasmid is a circular vector, the one or more sequences of the miRNA expression cassettes may be connected at the 3' end of SEQ ID NO. 1, as shown in SEQ ID NO. 7-11 or at the 5' end of SEQ ID NO. 1.

As will be appreciated by those skilled in the art, a perfect match of nucleotides with each of the miRNA expression cassette sequences is not necessary in order to have the desired result of decreased bioavailability of the target biomolecule as a result of the target cell producing the miRNA sequence that will bind to and degrade the mRNA of the target biomolecule. In some embodiments of the present disclosure, about 80% to about 100% nucleotide sequence matching with each of the miRNA expression cassettes causes the desired result. In some embodiments of the present disclosure, about 85% to about 100% nucleotide sequence matching with each of the miRNA expression cassettes causes the desired result. In some embodiments of the present disclosure, about 90% to about 100% nucleotide sequence matching with each of the miRNA expression cassettes causes the desired result. In some embodiments of the present disclosure, about 95% to about 100% nucleotide sequence matching with each of the miRNA expression cassettes causes the desired result.

Example 1—Expression Cassette

Expression cassettes for expressing miRNA were synthesized. The synthesized miRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each miRNA expression cassette was amplified by polymerase chain reaction (PCR) using Taq polymerase and the PCR products were gel purified and the bands on interest were also excised and purified using a gel extraction kit. These PCR products contained the miRNA expression cassettes in addition to 15 base pair 5' and 3' overhangs that aligned with the ends of the linearized pAVA-00200 backbone. Using in-fusion cloning, the amplified miRNA expression cassettes are integrated with the pAVA-00200 backbone via homologous recombination. The resulting RP contained the following: 5' ITR, CASI promoter, miRNA expression cassette, WPRE, SV40 polyA and ITR 3'.

The invention claimed is:

1. A composition that comprises a recombinant plasmid (RP) comprising a sequence of nucleotides that is SEQ ID NO: 7.

2. The composition of claim 1, wherein the RP is encapsulated in a protein coat, a lipid vesicle, or any combination thereof.

* * * * *